US00PP20985P2

(12) United States Plant Patent
Bartels

(10) Patent No.: US PP20,985 P2
(45) Date of Patent: May 11, 2010

(54) ROSE PLANT NAMED 'EMPARAIMP'

(50) Latin Name: *Rosa hybrida*
Varietal Denomination: Emparaimp

(75) Inventor: Gosen B. H. Bartels, Aalsmeer (NL)

(73) Assignee: Bartels Rose Breeding B.V., Aalsmeer (NL)

( * ) Notice: Subject to any disclaimer, the term of this patent is extended or adjusted under 35 U.S.C. 154(b) by 0 days.

(21) Appl. No.: 12/315,313

(22) Filed: Dec. 2, 2008

(51) Int. Cl.
*A01H 5/00* (2006.01)

(52) U.S. Cl. ..... Plt./134

(58) Field of Classification Search ..... Plt./104, Plt./134
See application file for complete search history.

*Primary Examiner*—June Hwu
(74) *Attorney, Agent, or Firm*—C. A. Whealy

(57) ABSTRACT

A new and distinct cultivar of Rose plant named 'Emparaimp', characterized by its long and upright flowering stems; strong plants; bright yellow-colored flowers; and excellent postproduction longevity.

1 Drawing Sheet

Botanical designation: *Rosa hybrida.*
Cultivar denomination: 'EMPARAIMP'.

BACKGROUND OF THE INVENTION

The present Invention relates to a new and distinct cultivar of Rose plant, botanically known as *Rosa hybrida*, commercially used as a cut flower Rose, and hereinafter referred to by the name 'Emparaimp'.

The new Rose plant is a product of a planned breeding program conducted by the Inventor in Aalsmeer, The Netherlands. The objective of the breeding program was to develop new freely-flowering cut flower Rose varieties with attractive flower colors and excellent postproduction longevity.

The new Rose plant is a naturally-occurring whole plant mutation of *Rosa hybrida* 'Empara', not patented. The new Rose was discovered and selected by the Inventor as a single flowering plant from within a population of plants of 'Empara' in a controlled greenhouse environment in Aalsmeer, The Netherlands in 2008.

Asexual reproduction of the new Rose by cuttings at Aalsmeer, The Netherlands, has shown that the unique features of this new Rose plant are stable and reproduced true to type in successive generations of asexual reproduction.

SUMMARY OF THE INVENTION

The following traits have been repeatedly observed and are determined to be the unique characteristics of 'Emparaimp'. These characteristics in combination distinguish 'Emparaimp' as a new and distinct Rose cultivar:

1. Long and upright flowering stems.
2. Strong plants.
3. Bright yellow-colored flowers.
4. Excellent postproduction longevity.

Plants of the new Rose differ from plants of the parent, 'Empara', primarily in flower bud size as plants of the new Rose have taller flower buds than plants of 'Empara'.

Plants of the new Rose can be compared to plants of *Rosa hybrida* 'Illios', not patented. In side-by-side comparisons conducted in Aalsmeer, The Netherlands, plants of the new Rose differed from plants of 'Illios' in the following characteristics:

1. Plants of the new Rose had larger leaves than plants of 'Illios'.
2. Plants of the new Rose had larger flowers with more petals per flower than plants of 'Illios'.
3. Plants of the new Rose had taller flower buds than plants of 'Illios'.
4. Flower color of plants of the new Rose did not fade, however flower color of plants of 'Illios' faded with development.

BRIEF DESCRIPTION OF THE PHOTOGRAPH

The accompanying colored photograph illustrates the overall appearance of the new Rose plant, showing the colors as true as it is reasonably possible to obtain in colored reproductions of this type. Colors in the photograph may differ slightly from the color values cited in the detailed botanical description which accurately describe the colors of the new Rose.

The photograph comprises a side perspective view of a typical flowering stem of 'Emparaimp'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown during the summer and early autumn in Aalsmeer, The Netherlands, in a glass-covered greenhouse and under commercial production practices. Plants had been growing for nine months when the photographs and description were taken. During the production of the plants, day temperatures averaged 20° C., night temperatures averaged 18° C. and light levels averaged 10 kilolux. In the following description, color references are made to The Royal Horticultural Society Colour Chart, 2001 Edition, except where general terms of ordinary dictionary significance are used.

Botanical classification: *Rosa hybrida* 'Emparaimp'.

Parentage: Naturally-occurring whole plant mutation of *Rosa hybrida* 'Empara', not patented.

Propagation:

*Type.*—By cuttings.

*Time to initiate roots.*—About ten days at 20° C.

*Time to produce a rooted young plant.*—About five weeks at 20° C.

*Root description.*—Fleshy, medium in thickness; white in color.

*Rooting habit.*—Freely branching; moderately dense.

Plant description:

*Plant form.*—Upright plant habit; long and upright flowering stems.

*Growth habit.*—Vigorous; freely basal branching habit; dense and bushy growth habit; about 25 to 30 flowering stems develop per year.

*Plant height.*—About 70 cm to 80 cm.

*Plant width* (*spread*).—About 30 to 40 cm.

*Lateral branches* (*peduncles*).—Length: About 70 cm to 80 cm. Diameter: About 7 mm to 8 mm. Internode length: About 5 cm to 7 cm. Strength: Strong. Texture: Pubescent. Color: Close to 138B becoming closer to 137C with development. Thorns: Shape: Triangular with sharp acuminate apices. Height: About 8 mm. Diameter, at base: About 6 mm. Color, immature and mature: Close to 173A.

Foliage description:

*Arrangement.*—Alternate; compound with typically three to seven leaflets per leaf.

*Terminal leaflet length.*—About 8 cm.

*Terminal leaflet width.*—About 5 cm.

*Lateral leaflet length.*—About 5 cm.

*Lateral leaflet width.*—About 4 cm.

*Leaflet shape.*—Ovate.

*Leaflet apex.*—Acuminate.

*Leaflet base.*—Obtuse.

*Leaflet margin.*—Serrate.

*Leaflet texture, upper and lower surfaces.*—Smooth, glabrous.

Leaflet venation pattern: Pinnate.

*Leaflet color.*—Developing leaflets, upper surface: Close to 137A. Developing leaflets, lower surface: Close to 138C. Fully expanded leaflets, upper surface: Close to 137A; venation, close to 138C and 60A. Fully expanded leaflets, lower surface: Close to 138A; venation, close to 138C and 60B.

*Petioles, leaves.*—Length: About 3 cm to 5 cm. Diameter: About 2.5 mm. Texture, upper and lower surfaces: Smooth, glabrous. Color, upper and lower surfaces: Close to 60C.

*Petioles, leaflets.*—Length: About 5 mm. Diameter: About 2 mm. Texture, upper and lower surfaces: Smooth, glabrous. Color, upper and lower surfaces: Close to 60C.

*Stipules.*—Quantity/arrangement/appearance: Two, adnate to the petiole, leafy. Length: About 3 cm. Width: About 2 mm. Shape: Lanceolate. Apex: Acuminate. Base: Truncate. Margin: Serrate. Texture, upper and lower surfaces: Smooth, glabrous. Venation pattern: Pinnate. Color, upper and lower surfaces: Close to 60C.

Flower description:

*Flower type and habit.*—Consistently symmetrical rosette flowers; one flower per terminal.

*Flowering season.*—Year-round under greenhouse conditions, optimal flowering from spring through autumn under garden conditions; flowering intermittent.

*Flower diameter.*—About 11 cm.

*Flower depth* (*height*).—About 5 cm.

*Flower longevity on plant.*—About 14 to 16 days; flowers persistent.

*Flower longevity as a cut flower.*—About 14 days.

*Fragrance.*—None detected.

*Flower buds.*—Shape: Ovoid. Length: About 4 cm to 5 cm. Diameter: About 3 cm to 4 cm. Color: Close to 7A.

*Petals.*—Quantity: Numerous; about 55 per flower. Length: About 5 cm. Width: About 5 cm. Shape: Broadly elliptical. Apex: Cuspidate. Base: Obtuse. Margin: Entire. Texture, upper and lower surfaces: Smooth, glabrous. Color: When opening, upper and lower surfaces: Close to 7A. Fully opened, upper and lower surfaces: Close to 7A; color does not fade with development.

*Sepals.*—Quantity per flower: Typically five. Length: About 4 cm. Width: About 1 cm. Shape: Lanceolate. Apex: Acuminate. Base: Obtuse. Margin: Entire. Texture, upper and lower surfaces: Smooth, glabrous. Color: When opening and fully opened, upper surface: Close to 138B. When opening and fully opened, lower surface: Close to 143C.

*Reproductive organs.*—Stamens: Quantity: About 60 per flower. Anther length: About 3 mm. Anther shape: Elliptical. Anther color: Close to 7A. Pollen amount: Scarce. Pistils: Quantity: About 50 per flower. Pistil length: About 1.2 cm. Stigma color: Close to 9C. Style length: About 8 mm. Style color: Close to 9C.

*Seeds/fruits.*—Seed and fruit development has not been observed on plants of the new Rose.

Pathogen/pest resistance: Plants the new Rose have been observed to be somewhat tolerant to Downy and Powdery Mildew. Plants of the new Rose have not been observed to be resist to pests and other pathogens common to Roses.

Temperature tolerance: Plants of the new Rose have been observed to tolerate temperatures ranging from 1° C. to 35° C.

It is claimed:

1. A new and distinct Rose plant named 'Emparaimp' as illustrated and described.

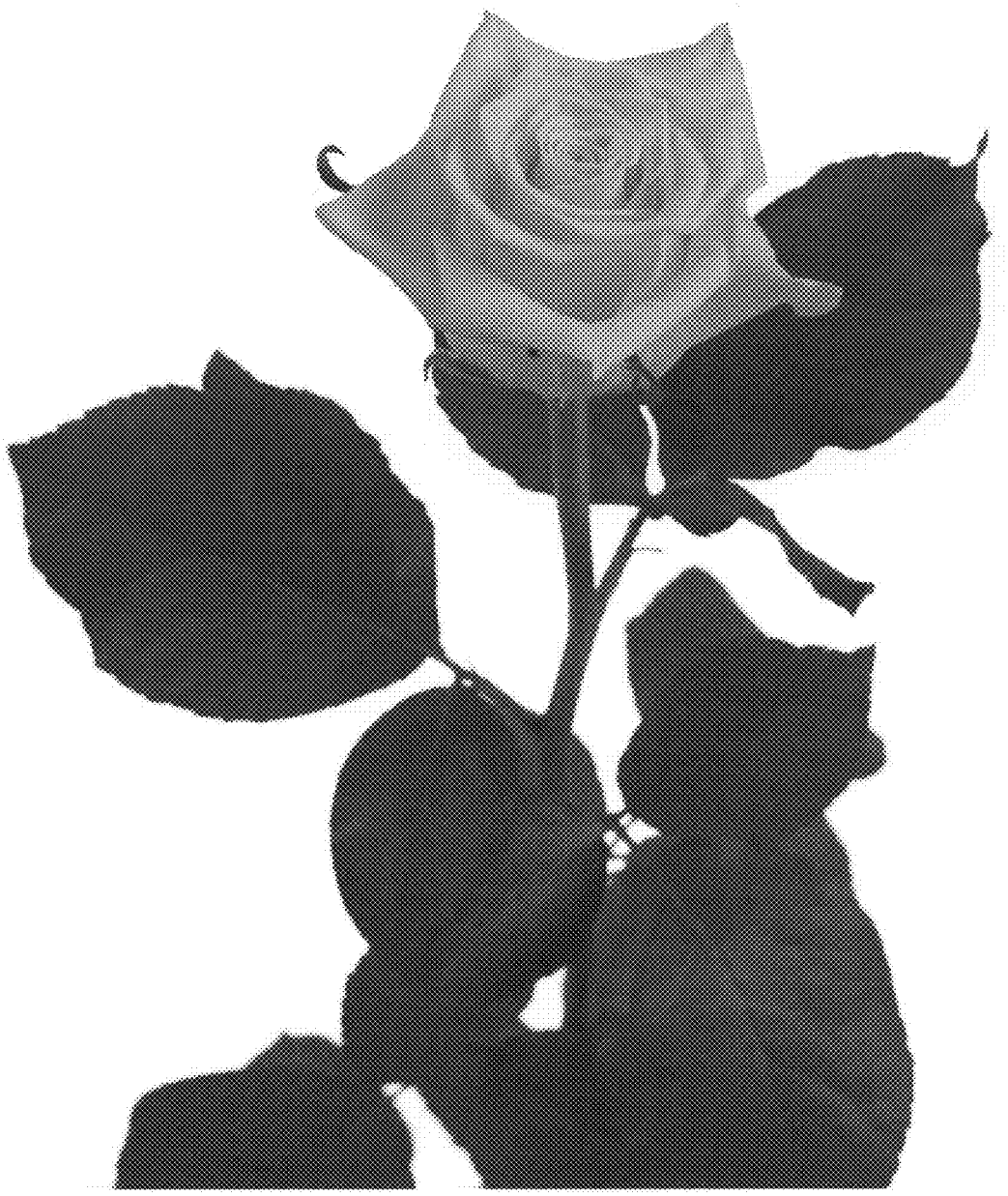

* * * * *